US011317637B2

(12) United States Patent
Mortensen

(10) Patent No.: US 11,317,637 B2
(45) Date of Patent: May 3, 2022

(54) PHOTO BIOREACTOR FOR COLD PASTEURIZATION OF LIQUID FOOD PRODUCTS AND THE USE OF THE REACTOR

(71) Applicant: LYRAS HOLDING APS, Nibe (DK)

(72) Inventor: Rasmus Mortensen, Aalborg (DK)

(73) Assignee: Lyras DK ApS, Aalborg (DK)

(*) Notice: Subject to any disclaimer, the term of this patent is extended or adjusted under 35 U.S.C. 154(b) by 7 days.

(21) Appl. No.: 16/649,028

(22) PCT Filed: Sep. 19, 2018

(86) PCT No.: PCT/DK2018/050230
§ 371 (c)(1),
(2) Date: Mar. 19, 2020

(87) PCT Pub. No.: WO2019/057257
PCT Pub. Date: Mar. 28, 2019

(65) Prior Publication Data
US 2020/0214306 A1    Jul. 9, 2020

(30) Foreign Application Priority Data

Sep. 21, 2017    (DK) .......................... PA 2017 70708

(51) Int. Cl.
*B01J 19/12*     (2006.01)
*C02F 1/32*      (2006.01)
(Continued)

(52) U.S. Cl.
CPC .......... *A23C 3/076* (2013.01); *B01J 19/0013* (2013.01); *B01J 19/123* (2013.01); *C02F 1/325* (2013.01); *B01J 2219/00051* (2013.01)

(58) Field of Classification Search
CPC .... B01J 19/123; B01J 19/243; B01J 19/0013; B01J 2219/00051; B01J 2219/0877;
(Continued)

(56) References Cited

U.S. PATENT DOCUMENTS 4,247,379 A * 1/1981 Leach .................... B01J 19/123
                                                204/157.41
5,034,235 A * 7/1991 Dunn ........................ A23L 3/28
                                                426/238
(Continued)

FOREIGN PATENT DOCUMENTS

CN    102318872 A    1/2012
EP    2 572 592 A1   3/2013
(Continued)

OTHER PUBLICATIONS

Who, "Ultraviolet Radiation" Nov. 26, 2016 <web.archive.org/web/20161126213207/http://www.who.int/uv/en/> (Year: 2016).*
(Continued)

*Primary Examiner* — Lessanework Seifu
(74) *Attorney, Agent, or Firm* — Crowell & Moring LLP; John C. Freeman, Esq.

(57) ABSTRACT

A system capable of a germicidal treatment of highly opaque liquids, featuring a filter, which prevents wavelengths above the UV-C spectrum reaching the liquid being treated, one or more spiral-shaped tubes extending from an inlet end to an outlet end creating a fluidic pathway, and one or more light sources illuminating the one or more spiral-shaped tubes, wherein the one or more light sources emit light in a wavelength range between 180-300 nm.

14 Claims, 11 Drawing Sheets

(51) Int. Cl.
  *A23C 3/07* (2006.01)
  *B01J 19/00* (2006.01)

(58) Field of Classification Search
  CPC .............. B01J 2219/0871; C02F 1/325; C02F 2201/3224; C02F 2201/3227; C02F 2201/3222; C02F 2301/022; C02F 2301/024; C02F 2301/026; C02F 2303/04; C02F 2307/14; A61L 2/10
  See application file for complete search history.

(56) References Cited

U.S. PATENT DOCUMENTS

| | | | | |
|---|---|---|---|---|
| 5,433,738 | A * | 7/1995 | Stinson | A61L 2/0011 250/435 |
| 5,547,590 | A * | 8/1996 | Szabo | B01J 19/123 210/103 |
| 2002/0096648 | A1 | 7/2002 | Kaiser et al. | |
| 2004/0222163 | A1 | 11/2004 | Saccomanno | |
| 2004/0248076 | A1 | 12/2004 | Kaiser et al. | |
| 2006/0045796 | A1 * | 3/2006 | Anderle | A61L 2/10 422/3 |
| 2008/0305018 | A1 | 12/2008 | Blum | |
| 2009/0145855 | A1 | 6/2009 | Day et al. | |
| 2010/0224562 | A1 | 9/2010 | Rolchigo et al. | |
| 2012/0261319 | A1 | 10/2012 | Shinagawa | |
| 2016/0046507 | A1 | 2/2016 | Deguchi et al. | |
| 2017/0101328 | A1 | 4/2017 | Smetona et al. | |
| 2017/0216466 | A1 * | 8/2017 | Dujowich | A61L 2/0047 |

FOREIGN PATENT DOCUMENTS

| | | | |
|---|---|---|---|
| KR | 101195588 | * | 10/2010 |
| WO | WO 2016/110829 A1 | | 7/2016 |

OTHER PUBLICATIONS

Machine Translation of KR 101195588 (Year: 2010).*
PCT/DK2018/050230 International Preliminary Report on Patentability dated Mar. 24, 2020 (eight pages).
Communication Pursuant to Article 94(3) EPC dated Feb. 12, 2021 (5 pages) from corresponding European Patent Application 18 780 023.0.
Article, Shah, S.H., "*Spectroscopic Analysis of Ultraviolet Lamps for Disinfection of Air in Hospitals*", Water Air Soil Pollut: Focus 9, pp. 529-537 (2009) https://doi.org/10.1007/s11267-009-9231-0.
Bandla, Srinivasarao et al.; "UV-C treatment of soymilk in coiled tube UV reactors for inactivation of *Escherichia coli* W1485 and Bacillus cereus endospores" Elsevier, LWT—Food Science and Technology; V46, No. 1; 2012; pp. 71-76, Academic Press; United Kingdom.
Shah, Nor Nadiah Abdul Karim et al.; "Fruit Juice Production Using Ultraviolet Pasteurization: A Review"; Beverages, MDPI; V2, No. 3, Aug. 5, 2016; 20p.
International Search Report and Written Opinion for priority application PCT/DK2018/050230; dated Nov. 7, 2018; 12 pages.
Schmidt, Sebastian et al.; "Process and Laboratory Scale UV Inactivation of Viruses and Bacteria Using an Innovative Coiled Tube Reactor"; Chemical Engineering & Technology; V. 30, No. 7; 2007; pp. 945-950.

* cited by examiner

PHOTO BIOREACTOR FOR COLD PASTEURIZATION OF LIQUID FOOD PRODUCTS AND THE USE OF THE REACTOR

This application is a National Stage application of International Application No. PCT/DK2018/050230, filed Sep. 19, 2018, the entire contents of which are incorporated herein by reference.

This application claims priority under 35 U.S.C. § 119(a) to Danish Patent Application No. PA 2017 70708, filed on Sep. 21, 2017, the entire contents of each of which are incorporated herein by reference.

BACKGROUND OF THE INVENTION

Field of the Invention

The invention relates to a photo bioreactor, which enables a germicidal treatment of liquids utilizing UV-C light, primarily in the wavelength between 180 nm to 300 nm. The invention relates to a system capable of germicidal treatment of highly opaque liquids.

Description of the Related Art

UV-reactor instruments have previous been used for pasteurization of liquid food products. Examples of such instruments can be found in US 2002/096648 or Chem. Eng. Technol. 2007, 30, pages 945-950, which both discloses a reactor for irradiating ultraviolet light into a fluid reaction medium. An irradiation chamber is connected to an inlet and an outlet which allows the reaction medium to flow through the reactor while being exposed to ultraviolet light.

Another example of such an UV-reactor instrument is US 2004/248076, which discloses an apparatus and process for sterilization of liquid media by means of UV irradiation and short-time heat treatment.

However, there is a need within the field for optimizing the killing of bacteria and viruses (i.e. pasteurization or sterilization) while avoiding or lowering the oxidation of the liquid product. Oxidation of the liquid product will result in an enhanced bitter and bad flavor/taste of the food product.

SUMMARY OF THE INVENTION

The present invention relates to an UV-reactor instrument for cold pasteurization of liquid food products. Thus, disclosed in a first aspect of the present invention is a photo bioreactor for cold pasteurization of liquid food products, e.g. milk, the photo bioreactor comprising:
  a. one or more spiral-shaped tubes extending from an inlet end to an outlet end creating a fluidic pathway, and
  b. one or more light sources illuminating the one or more spiral-shaped tubes, wherein the one or more light sources emit light in a wavelength range between 180-300 nm,
  wherein the photo bioreactor further comprises one or more filters positioned between the one or more light sources and the one or more spiral-shaped tubes, wherein the one or more filters prevent light above a wavelength of 300 nm from reaching the one or more spiral-shaped tubes.

By preventing light above a wavelength of 300 nm from reaching the one or more spiral-shaped tubes is meant that light above 300 nm is attenuated by a substantial amount, e.g. at least a factor of 100, or a factor of 1,000 or more.

In one or more embodiments, the one or more filters prevent light above a wavelength of 270 nm from reaching the one or more spiral-shaped tubes.

One of the advantages of using light radiation as a means for cold pasteurization is that it is a very energy efficient way for partial sterilization.

One of the advantages using one or more filter is that photo oxidation from higher wavelengths may be avoided. E.g. avoiding photo oxidation of riboflavin (around a wavelength of 446 nm) is preferred, but also avoiding photo oxidation of other components in the liquid food product, which enhances a bitter and bad flavor/taste in said food product, is preferred. Additionally, the filters may avoid hot air from contacting the one or more spiral-shaped coils, hereby avoiding heating of the liquid food product.

The fluidic pathway is designed to provide a high surface to volume ratio, increasing the exposure of light energy per unit volume with reduced self-shadowing effects from the opaque liquid being treated. In this manner it is possible to treat opaque liquids using light when the material, creating the fluidic pathway, is transparent to the radiation of light.

The liquid food product flows through the one or more spiral-shaped tubes with a flow rate. In one or more embodiments, the flow rate measured in millilitres per minutes is between 200-6,000 ml/min, or between 500-4,000 ml/min, or between 800-2,000 ml/min, or between 900-1,100 ml/min.

In one or more embodiments, the one or more light sources are a low pressure germicidal lamp, such as a low-pressure mercury-vapor lamp.

In one or more embodiments, the one or more light sources operate at a lamp temperature between 0° C. and 120° C.

In one or more embodiments, the one or more light sources operate at a lamp temperature between 20° C. and 60° C.

In one or more embodiments, the one or more light sources operate at a lamp temperature between 30° C. and 50° C.

Disclosed herein in a second aspect of the present invention is the use of a photo bioreactor as described throughout this document for cold pasteurization of liquid food products.

Cold pasteurization may be partial sterilization of a substance and especially a liquid in a process where heat is evaded as the main eradication of objectionable organisms without major chemical alteration of the substance. With evaded is not meant excluded but reduced.

In one or more embodiments, a biological contaminant is inactivated or reduced by an order of at least 2-$\text{Log}_{10}$. A biological contaminant may be e.g., bacteria, spores, mold, or virus.

In one or more embodiments, a biological contaminant is inactivated or reduced by an order of at least 3-$\text{Log}_{10}$.

In one or more embodiments, a biological contaminant is inactivated or reduced by an order of at least 4-$\text{Log}_{10}$.

In one or more embodiments, a biological contaminant is inactivated or reduced by an order of at least 5-$\text{Log}_{10}$.

In one or more embodiments, a biological contaminant is inactivated or reduced by an order of at least 6-$\text{Log}_{10}$.

Disclosed herein in a third aspect of the present invention is the use of a photo bioreactor as described throughout this document for killing microorganisms in liquid food products, such as bacteria, mold, spores, or virus.

With killing is meant reducing the amount of active or living microorganisms. Microorganisms found in liquid food products may be present due to contamination during the process of said liquid food product. Common bacteria contamination of e.g. dairy products may be e.g., *Lactobacillus casei, Escherichia coli, Listeria monocytogenes, Salmonella* spp., *Mycobacterium avium* subspecies paratuberculosis (MAP), *Staphylococcus aureus*, or *Streptococcus* spp.

The invention relates to a photo bioreactor comprising a filter blocking ultraviolet light above 300 nm, and further to a hydraulic design, which enables a germicidal treatment of liquids utilizing UV-C light, ranging from 180 nm to 300 nm.

The invention relates to a system capable of a germicidal treatment of highly opaque liquids. The invention comprises a filter, which prevents wavelengths above the UV-C spectrum from reaching the liquid being treated. The filter channels an optional airflow over the one or more light sources. In this manner, the airflow is prevented from reaching a reactor chamber, in which the liquid product is being treated, while maintaining the light sources at their optimal operational temperature. Furthermore, the invention relates to a hydraulic design involving one or more coiled spiral-shaped tubes, which enables crossflows, due to a centrifugal force. This enables most opaque liquids to be treated using UV-C light.

In describing the aspects of the invention specific terminology will be used for the sake of clarity. However, the invention is not intended to be limited to the specific terms so selected, and it is understood that each specific term includes all technical equivalents which operate in a similar manner to accomplish a similar purpose.

Disclosed in a first aspect of the present invention is a photo bioreactor for cold pasteurization of liquid food products, e.g. milk, the photo bioreactor comprising:
a. one or more spiral-shaped tubes extending from an inlet end to an outlet end creating a fluidic pathway, and
b. one or more light sources illuminating the one or more spiral-shaped tubes, wherein the one or more light sources emit light in a wavelength range between 180-300 nm,
wherein the photo bioreactor further comprises one or more filters positioned between the one or more light sources and the one or more spiral-shaped tubes, wherein the one or more filters prevent light above a wavelength of 300 nm from reaching the one or more spiral-shaped tubes.

Pasteurization is not only limited to partial sterilization of a substance and especially a liquid at a temperature and for a time period of exposure that destroys objectionable organisms without major chemical alteration of the substance, but also covers cold pasteurization which is partial sterilization of a substance and especially a liquid in a process where heat is evaded as the main eradication of objectionable organisms without major chemical alteration of the substance. With evaded is not meant excluded but reduced. The present invention discloses that one of the advantages of using light radiation as a means for cold pasteurization is that it is a very energy efficient way for partial sterilization.

The fluidic pathway is designed to provide a high surface to volume ratio, increasing the exposure of light energy per unit volume with reduced self-shadowing effects from the opaque liquid being treated. In this manner it is possible to treat opaque liquids using light when the material, creating the fluidic pathway is transparent to the radiation of light.

The one or more spiral-shaped tubes extending from an inlet end to an outlet end creating a fluidic pathway utilizes the flow regime occurring when the media is traveling in the fluidic pathway. The flow regime in the fluidic pathway may consists of one or several eddies, which creates a secondary flow axial on the primary flow utilizing the centrifugal force (e.g. Dean vortex flow) to enhance the surface of the liquid being exposed to UV-light emitted by the light sources.

The fluid movement through the fluidic pathway may have a double vortexual pattern consistent with a Dean vortex flow. This provides an axial flow in the fluidic pathway, providing a high surface to volume ratio. This may increase the exposure of light energy per unit volume/ surface area with reduced self-shadowing effects from the opaque liquid being treated.

In one or more embodiments, a fluid movement through the one or more spiral-shaped tubes creates a Dean Vortex flow, laminar flow, or turbulent flow.

The present invention discloses that one of the advantages using a Dean Vortex, laminar, or turbulent flow, is that it may increase the exposure of light energy per unit volume/ surface area with reduced self-shadowing effects from the opaque liquid being treated, hereby using less energy and time for treatment of the same volume.

Between the one or more spiral-shaped tubes and the one or more light sources may be located one or more filters to narrow the wavelength of the light radiated to the one or more spiral-shaped tubes to a narrower band. This will ensure an optimal wavelength for killing bacteria and viruses while avoiding oxidation of the liquid food product (see FIG. 11).

By preventing light above a wavelength of 300 nm from reaching the one or more spiral-shaped tubes is meant that light above 300 nm is attenuated by a substantial amount, e.g. at least a factor of 100, or a factor of 1000 or more.

In one or more embodiments, the one or more filters prevent light above a wavelength of 290 nm from reaching the one or more spiral-shaped tubes.

In one or more embodiments, the one or more filters prevent light above a wavelength of 280 nm from reaching the one or more spiral-shaped tubes.

In one or more embodiments, the one or more filters prevent light above a wavelength of 270 nm from reaching the one or more spiral-shaped tubes.

In one or more embodiments, the one or more filters prevent light above a wavelength of 260 nm from reaching the one or more spiral-shaped tubes.

In one or more embodiments, a cross-section shape of the one or more spiral-shaped tubes is circular, hexagonal, square, triangular, or oval. The cross-section shape may have any shape, which will still maintain a large exposed outer area of the liquid food product.

In one or more embodiments, the one or more spiral-shaped tubes have an inner tube diameter between 1 mm and 10 mm.

In one or more embodiments, the one or more spiral-shaped tubes have an inner tube diameter between 2 mm and 9 mm.

In one or more embodiments, the one or more spiral-shaped tubes have an inner tube diameter between 3 mm and 8 mm.

In one or more embodiments, the one or more spiral-shaped tubes have an inner tube diameter between 4 mm and 7 mm.

In one or more embodiments, the one or more spiral-shaped tubes have an inner tube diameter between 5 mm and 6 mm.

In one or more embodiments, the one or more spiral-shaped tubes have an inner tube diameter of 5.5 mm.

The size of the inner diameter is a tradeoff between the amounts of liquid food product capable of being treated over a given time versus the exposure of light energy per unit volume/surface area. The larger the inner tube diameter is the more liquid food product can pass over any given time, however, the larger the inner diameter is the smaller (relatively seen) the exposed area may be.

In one or more embodiments, the one or more spiral-shaped tubes have a pitch between 2 and 8 mm, wherein the pitch is the distance from center to center of the one or more spiral-shaped tubes after one turn/coil of the one or more spiral-shaped tubes.

In one or more embodiments, the one or more spiral-shaped tubes have a pitch between 3 and 7 mm, wherein the pitch is the distance from center to center of the one or more spiral-shaped tubes after one turn/coil of the one or more spiral-shaped tubes.

In one or more embodiments, the one or more spiral-shaped tubes have a pitch between 4 and 7 mm, wherein the pitch is the distance from center to center of the one or more spiral-shaped tubes after one turn/coil of the one or more spiral-shaped tubes.

In one or more embodiments, the one or more spiral-shaped tubes have a pitch of 6 mm, wherein the pitch is the distance from center to center of the one or more spiral-shaped tubes after one turn/coil of the one or more spiral-shaped tubes.

In one or more embodiments, the one or more spiral-shaped tubes have a coil angle between 1° and 6°, such as between 2° and 5°, such as between 3° and 4°, wherein the coil angle is measured between the one or more spiral-shaped tubes and a straight direction compared to the inlet end to the outlet end creating the fluidic pathway.

In one or more embodiments, the one or more spiral-shaped tubes have a coil angle between 2° and 5°.

In one or more embodiments, the one or more spiral-shaped tubes have a coil angle between 3° and 4°.

In one or more embodiments, the one or more spiral-shaped tubes have a coil diameter between 20 and 150 mm, wherein the coil diameter is a distance from outer end to outer end of the one or more spiral-shaped tubes after a half turn/coil of the one or more spiral-shaped tubes. That is, the coil diameter is the width of a coil created by the one or more spiral-shaped tubes.

In one or more embodiments, the one or more spiral-shaped tubes have an outer tube diameter between 2 and 8 mm. In one or more embodiments, the one or more spiral-shaped tubes have an outer tube diameter of between 5 and 6 mm.

In one or more embodiments, the one or more spiral-shaped tubes have an outer tube diameter between 3 and 7 mm.

In one or more embodiments, the one or more spiral-shaped tubes have an outer tube diameter between 4 and 7 mm.

In one or more embodiments, the one or more spiral-shaped tubes have an outer tube diameter of between 5 and 6 mm.

In one or more embodiments, the one or more spiral-shaped tubes have an outer tube diameter of 6 mm.

In one or more embodiments, the one or more spiral-shaped tubes have a wall thickness between 0.1 and 0.4 mm. The wall thickness may also be defined as the outer tube diameter minus the inner tube diameter.

In one or more embodiments, the one or more spiral-shaped tubes have a wall thickness between 0.1 and 0.3 mm.

In one or more embodiments, the one or more spiral-shaped tubes have a wall thickness between 0.2 and 0.3 mm.

In one or more embodiments, the one or more spiral-shaped tubes have a wall thickness between 1 and 4 mm.

In one or more embodiments, the one or more spiral-shaped tubes have a wall thickness between 1 and 3 mm.

In one or more embodiments, the one or more spiral-shaped tubes have a wall thickness between 2 and 3 mm.

A wall thickness between 0.1 and 4 mm is mostly used when the one or more spiral-shaped tubes are made of polymeric material, whereas the wall thickness of 1 to 4 mm is mostly used when quartz glass is used for the one or more spiral-shaped tubes. However, the wall thickness of the one or more tubes depends on the transmission percentage of the light emitted by the one or more light sources. The higher the transmission percentage, the thicker the walls can be made.

In one or more embodiments, the one or more spiral-shaped tubes are coiled around a pillar.

One advantage using a pillar to coil the one or more spiral-shaped tubes around is that a pillar stabilizes the one or more spiral-shaped tubes, if said tubes are e.g. made of a flexible material. The pillar may hence provide stabilization for the coil. Additionally, the pillar may have other advantage, e.g. helping with enhancing the amount of light radiated to the one or more spiral-shaped tubes by being e.g. reflective.

In one or more embodiments, the one or more spiral-shaped tubes are coiled around a pillar so as to create a cone shaped coil. This means that the start of the coil is narrower than the end of the coil, or that the start of the coil is wider than the end of the coil. This may yield a pyramidal shaped coil.

In one or more embodiments, the one or more spiral-shaped tubes include only one spiral-shaped tube. In another embodiment, the one or more spiral-shaped tubes are coiled around a pillar in pairs of at least two.

In one or more embodiments, the pillar is made of a reflective material.

Reflective material may be, but is not limited to, dichroic reflector material, such as aluminum, stainless steel, chromium, or silver.

Reflective material may also be partly reflective materials such as Teflon materials, such as perfluoroalkoxy alkanes (PFA), polytetrafluoroethylene (PTFE), fluorinated ethylene propylene (FEP). The reflectiveness of such materials depends on the angle of the light emission on the material.

Polytetrafluoroethylene (PTFE) is a synthetic fluoropolymer of tetrafluoroethylene that has numerous applications. The best known brand name of PTFE-based formulas is Teflon. PTFE is a fluorocarbon solid, as it is a high-molecular-weight compound consisting wholly of carbon and fluorine. PTFE is hydrophobic: neither water nor water-containing substances wet PTFE, as fluorocarbons demonstrate mitigated London dispersion forces due to the high electronegativity of fluorine. PTFE has one of the lowest coefficients of friction of any solid.

Perfluoroalkoxy alkanes (PFA) are fluoropolymers. They are copolymers of tetrafluoroethylene ($C_2F_4$) and perfluoroethers ($C_2F_3OR_f$, where $R_f$ is a perfluorinated group such as e.g. trifluoromethyl ($CF_3$)). The properties of PFA are similar to PTFE. One of the big differences is that the alkoxy substituents allow the polymer to be e.g. melt-processed. On a molecular level, PFA has a smaller chain length, and higher chain entanglement than other fluoropolymers. It also contains an oxygen atom at the branches. This results in a material that is more translucent and has improved flow, creep resistance, and thermal stability close to or exceeding PTFE.

Fluorinated ethylene propylene (FEP) is a copolymer of hexafluoropropylene and tetrafluoroethylene. It differs from the PTFE in that it is melt-processable using conventional injection molding and screw extrusion techniques. Fluorinated ethylene propylene is sold under the brand name Teflon FEP. Other brand names are Neoflon FEP or Dyneon FEP. FEP is very similar in composition to the fluoropolymers PTFE and PFA. FEP is softer than PTFE and melts around 260° C. FEP is highly transparent and resistant to sunlight.

FEP and PFA both share PTFE's useful properties of low friction and non-reactivity, but are more easily formable.

In one or more embodiments, the pillar is made of a reflective polymeric material.

In one or more embodiments, the pillar is covered with a metallized film.

Metalized films are polymer films coated with a thin layer of metal, such as, but not limited to, aluminum. They offer the glossy metallic appearance of an aluminum foil at a reduced weight and cost.

In one or more embodiments, the pillar is made of polytetrafluoroethylene (PTFE).

In one or more embodiments, the pillar is the one or more light sources.

In one or more embodiments, the one or more spiral-shaped tubes have a compressed length from the inlet end to the outlet end between 100 mm and 400 mm. The compressed length is the length of the one or more spiral-shaped tubes as shaped in the photo bioreactor without pulling or pressing on the one or more spiral-shaped tubes, so as to get a measure from the inlet to the outlet end.

In one or more embodiments, the one or more spiral-shaped tubes have an extension/free length from the inlet end to the outlet end between 5 m and 20 m. The extension/free length is the total length of one tube in the one or more spiral-shaped tubes. The total length of one tube is equal to the total distances one liquid food product unit has to pass through the one or more spiral-shaped tubes.

In one or more embodiments, the one or more spiral-shaped tubes are made of a polymeric or quartz glass material being ultraviolet light transparent. However, the one or more spiral-shaped tubes can be made of any material as long as said material is more or less transparent to the light emitted by the one or more light sources.

In one or more embodiments, the one or more spiral-shaped tubes are selected from fluorinated ethylene propylene (FEP), polytetrafluoroethylene (PTFE), or perfluoroalkoxy alkanes (PFA). The one or more spiral-shaped tubes may be made of any materiel with similar properties of FEP, PTFE, or PFA.

In one or more embodiments, the one or more spiral-shaped tubes are from amorphous fluoropolymer (AF). The one or more spiral-shaped tubes may be made of any materiel with similar properties of AF.

Amorphous fluoropolymer (AF) is a family of amorphous fluoroplastics. These materials are similar to other amorphous polymers in optical clarity and mechanical properties, including strength. These materials are comparable to other fluoroplastics in their performance over a wide range of temperatures, in having excellent chemical resistance, and in having outstanding electrical properties. AF polymers are distinct from other fluoroplastics in that they are soluble in selected solvents, have high gas permeability, high compressibility, high creep resistance, and low thermal conductivity. AF polymers have the lowest dielectric constant of any known solid polymer. AF polymers have a low index of refraction when compared to many other known polymer.

In one or more embodiments, the inlet end and the outlet end is designed such that the liquid food product enters and exits the one or more spiral-shaped tubes axially. This means that liquid will exit from the outlet end more or less axially to where it entered in the inlet end.

In one or more embodiments, the inlet end and the outlet end is designed such that the liquid food product flows overall vertically through the one or more spiral-shaped tubes when observing from inlet end to outlet end. This means that the liquid food product will enter the one or more spiral-shaped tubes through the inlet vertically, flow through the one or more spiral-shaped tubes, and exit the outlet vertically, hereby giving an overall vertical flow.

In one or more embodiments, the inlet end and the outlet end is designed such that the liquid food product flows overall horizontally through the one or more spiral-shaped tubes when observing from inlet to outlet. This means that the liquid food product will enter the one or more spiral-shaped tubes through the inlet horizontally, flow through the one or more spiral-shaped tubes, and exit the outlet horizontally, hereby giving an overall horizontal flow.

In one or more embodiments, the one or more light sources are coupled to one or more fibers guiding the 180-300 nm light from the one or more light sources to the one or more spiral-shaped tubes. This means that the light emitted from the light source is guided via/through one or more fibers to the one or more spiral-shaped tubes. A fiber may be an optical fiber. An optical fiber is a flexible, transparent fiber made by e.g., drawing glass (silica) or plastic to a chosen diameter. Optical fibers may be used as a means to transmit light between the two ends of the fiber.

In one or more embodiments, one light source and multiple fibers are used for illuminating the one or more spiral-shaped tubes.

In one or more embodiments, the one or more light sources are selected from a mercury-vapor lamp, xenon lamp, or a light emitting diode (LED). The light source of the present invention may be any light source suitable for creating light emission in the spectral wavelength area of 180 nm to 300 nm.

A mercury-vapor lamp is a gas discharge lamp that uses an electric arc through vaporized mercury to produce light. The arc discharge may be confined to a small fused quartz arc tube.

A light emitting diode (LED) is a two-lead semiconductor light source. It is a p-n junction diode that emits light when activated. When a suitable voltage is applied to the leads, electrons are able to recombine with electron holes within the device, releasing energy in the form of photons. This effect is called electroluminescence, and the color of the light (corresponding to the energy of the photon) is determined by the energy band gap of the semiconductor. LEDs are typically small (less than 1 mm) and integrated optical components may be used to shape the radiation pattern.

A xenon arc lamp is a specialized type of gas discharge lamp, an electric light that produces light by passing electricity through ionized xenon gas at high pressure. It produces a bright white light that closely mimics natural sunlight. A special kind of xenon lamp is used in automobiles. These are actually metal-halide lamps, where a xenon arc is only used during start-up.

In one or more embodiments, the one or more light sources are a metal-halide lamp. A metal-halide lamp is an electrical lamp that produces light by an electric arc through a gaseous mixture of vaporized mercury and metal halides. It is a type of high-intensity gas discharge lamp. They are similar to mercury-vapor lamps, but contain additional metal halide compounds in the quartz arc tube, which may improve the efficiency and color rendition of the light.

In one or more embodiments, the one or more light sources are selected from a light source emitting light in the ultraviolet C (UV-C) spectral wavelength area.

The ultraviolet spectra may be broken down into several smaller areas, these are: ultraviolet A (UV-A), 315-400 nm; ultraviolet B (UV-B), 280-315 nm; ultraviolet C (UV-C), 100-280 nm; near ultraviolet (N-UV), 300-400 nm; middle ultraviolet (M-UV), 200-300 nm; far ultraviolet (F-UV), 122-200 nm.

In one or more embodiments, the one or more light sources are selected from a light source emitting light in the middle ultraviolet (M-UV) spectral wavelength area.

In one or more embodiments, the one or more light sources are a low pressure germicidal lamp, such as a low-pressure mercury-vapor lamp.

A low pressure germicidal lamp may be a UV lamp that emits a significant portion of its radiative power in the UV-C band, such as a low-pressure mercury-vapor lamp or a low pressure amalgam lamp.

A low pressure amalgam lamp is a lamp doped with mercury combined with another element (often gallium) and hence is also called an amalgam lamp.

In one or more embodiments, the one or more light sources operate at a lamp temperature between 0° C. and 120° C.

In one or more embodiments, the one or more light sources operate at a lamp temperature between 20° C. and 60° C.

In one or more embodiments, the one or more light sources operate at a lamp temperature between 30° C. and 50° C.

The present invention discloses that one of the advantages by utilizing a light source with a lower lamp temperature may be that less heat is transferred from the light source to the liquid food product. This may yield a lower requirement for cooling of the liquid food product during operation of the bioreactor.

In one or more embodiments, the one or more light sources operate at a lamp temperature of 40° C.

In one or more embodiments, the one or more light sources are positioned on the outside of the one or more spiral-shaped tubes.

In another embodiment the one or more light sources are positioned on the inside of the one or more spiral-shaped tubes. In yet other embodiments, the one or more light sources are positioned both on the inside of the one or more spiral-shaped tubes and on the outside of the one or more spiral-shaped tubes.

The positioning of the one or more light sources can be varied according to the overall setup of the bioreactor to achieve the highest possible transfer of energy from the one or more light sources to the liquid food product inside the one or more spiral-shaped tubes.

In one or more embodiments, the one or more filters are selected from bandpass filters, notch filters, or a combination of both.

One of the advantages using one or more filter (e.g. a bandpass filter or a notch filter) may be that photo oxidation from higher wavelengths may be avoided. E.g. avoiding photo oxidation of riboflavin (around a wavelength of 446 nm) is preferred, but also avoiding photo oxidation of other components in the liquid food product, which enhances a bitter and bad flavor/taste in said food product, is preferred. Additionally, the filters may avoid hot air from contacting the one or more spiral-shaped coils, hereby avoiding heating of the liquid food product.

A bandpass filter is a device that passes frequencies within a certain range and rejects/attenuates frequencies outside that range.

A notch filter is a band-stop filter with a narrow stopband. In signal processing, a band-stop filter or band-rejection filter is a filter that passes most frequencies unaltered, but rejects/attenuates those in a specific range to very low levels. It is the opposite of a band-pass filter.

In one or more embodiments, the photo bioreactor further comprises a reactor housing. The reactor housing is modularly designed, and hence does not have a minimum or maximum length. The size of the reactor housing depends on the size of the one or more light sources, the one or more spiral-shaped tubes, and other features added to the bioreactor. A reactor housing may be desirable as it will contain the light inside the reactor and reflect the light back towards the one or more spiral-shaped tubes.

In one or more embodiments, the one or more spiral-shaped tubes, the one or more light sources, and the one or more filters are enclosed inside the reactor housing.

In one or more embodiments, the reactor housing is made of a UV-C reflective material. A UV-C reflective material may be a material, which reflects light emitted in the spectral area of 100 nm to 300 nm. By utilizing a reflective UV-C material one advantage may be minimization of the energy needed for reactor to run, as more of the light may be reflected back towards the one or more spiral-shaped tubes.

In one or more embodiments, the reactor housing is made of reflective polytetrafluoroethylene (PTFE).

Polytetrafluoroethylene (PTFE) is a synthetic fluoropolymer of tetrafluoroethylene that has numerous applications. The best known brand name of PTFE-based formulas is Teflon. PTFE is a fluorocarbon solid, as it is a high-molecular-weight compound consisting wholly of carbon and fluorine. PTFE is hydrophobic: neither water nor water-containing substances wet PTFE, as fluorocarbons demonstrate mitigated London dispersion forces due to the high electronegativity of fluorine. PTFE has one of the lowest coefficients of friction of any solid.

In one or more embodiments, the photo bioreactor further comprises means for air cooling of the one or more light sources. Depending on the lamp temperature additional cooling may be needed to keep the liquid food product at an acceptable temperature while traveling through the fluidic pathway.

In one or more embodiments, a flow of air for cooling the light sources is a flow air from side to side of the photo bioreactor.

In one or more embodiments, a flow of air for cooling the light sources is a flow air from the top of the photo bioreactor to the bottom of the photo bioreactor. Alternatively, the flow may be from bottom to top, or a combination of flow from side to side and bottom/top to top/bottom.

The flow of air for cooling of lamps may be adjusted in multiple ways to optimally cool the lamps to a required temperature. Air may also flow through the middle section of the lamps for an optimal cooling.

In one or more embodiments, the photo bioreactor further comprises a control unit.

A control unit may be a unit capable of measuring and controlling e.g., flow speed, temperature, light intensity and various other properties. One of the advantages using a control unit may be an automatic control of the bioreactor. Additionally, with a control unit, a surveillance system may be setup, so that if e.g. the pressure is decreasing, the temperature is increasing, or the light intensity is decreasing, the operator may be notified.

In one or more embodiments, the control unit comprises electronic temperature control and flow control.

In one or more embodiments, the control unit automatically controls the lamp temperature and a flow speed of a liquid through the fluidic pathway. Utilizing automatic control may have one of the advantages of the user saving time due to less time spend observing the system and doing manual controlled adjustments of the properties of the system. Additionally, with a control unit, a surveillance system may be setup, so that if e.g. the pressure is decreasing, the temperature is increasing, or the light intensity is decreasing, the operator may be notified.

Additionally, the control unit may automatically counter the decrease in pressure, the increase in temperature, or the decrease in light intensity. Alternatively, the control unit may shut down the reactor if not able to counter the different irregularities.

Another aspect of the present invention is the use of a photo bioreactor as described throughout this document for cold pasteurization of liquid food products.

Cold pasteurization may be partial sterilization of a substance and especially a liquid in a process where heat is evaded as the main eradication of objectionable organisms without major chemical alteration of the substance. With evaded is not meant excluded but reduced. The present invention discloses that one of the advantages of using light radiation as a means for cold pasteurization is that it is a very energy efficient way for partial sterilization.

In one or more embodiments, the liquid food products are selected from liquid dairy products.

In one or more embodiments, the liquid food products are selected from raw milk, milk, juice, coffee, tea, soya, soylent, soda, broth, soup, beer, smoothies, protein shake, liquid meal-replacement, cream, wine, mayonnaise, ketchup, syrup, honey, or opaque processing water.

In one or more embodiments, a biological contaminant is inactivated or reduced by an order of at least 2-$Log_{10}$. A biological contaminant may be e.g., bacteria, spores, mold, or virus.

In one or more embodiments, a biological contaminant is inactivated or reduced by an order of at least 3-$Log_{10}$.

In one or more embodiments, a biological contaminant is inactivated or reduced by an order of at least 4-$Log_{10}$.

In one or more embodiments, a biological contaminant is inactivated or reduced by an order of at least 5-$Log_{10}$.

In one or more embodiments, a biological contaminant is inactivated or reduced by an order of at least 6-$Log_{10}$.

In one or more embodiments, the biological contaminant is selected from *Campylobacter jejuni, Shigella, Coxiella burnetii, Escherichia coli, Listeria monocytogenes, Mycobacterium bovis, Mycobacterium tuberculosis, Mycobacterium paratuberculosis, Salmonella* spp., *Yersinia enterocolitica, Brucella* spp., *Staphylococcus* spp., *Lactobacillus casei, Mycobacterium avium* subspecies, *Staphylococcus aureus, Streptococcus* spp., *Enterococcus* spp., or *Entrerobacter* spp.

Another aspect of the present invention is the use of a photo bioreactor as described throughout this document for killing microorganisms in liquid food products, such as bacteria, mold, spores, or virus.

With killing is meant reducing the amount of active or living microorganisms. Microorganisms found in liquid food products may be present due to contamination during the process of said liquid food product. Common bacteria contamination of e.g. dairy products may be e.g., *Lactobacillus casei, Escherichia coli, Listeria monocytogenes, Salmonella* spp., *Mycobacterium avium* subspecies paratuberculosis (MAP), *Staphylococcus aureus*, or *Streptococcus* spp.

In one or more embodiments, the liquid food products are selected from liquid dairy products.

In one or more embodiments, the liquid food products are selected from raw milk, milk, juice, coffee, tea, soya, soylent, soda, broth, soup, beer, smoothies, protein shake, liquid meal-replacement, cream, wine, mayonnaise, ketchup, syrup, honey, or opaque processing water.

In one or more embodiments, a biological contaminant is inactivated or reduced by an order of at least 2-$Log_{10}$, such as at least 3-$Log_{10}$, such as at least 4-$Log_{10}$, such as at least 5-$Log_{10}$, such as at least 6-$Log_{10}$. A biological contaminant may be e.g., bacteria, spores, mold, or virus.

In one or more embodiments, a biological contaminant is inactivated or reduced by an order of at least 5-$Log_{10}$.

In one or more embodiments, a biological contaminant is inactivated or reduced by an order of at least 6-$Log_{10}$.

In one or more embodiments, the biological contaminant is selected from *Campylobacter jejuni, Shigella, Coxiella burnetii, Escherichia coli, Listeria monocytogenes, Mycobacterium bovis, Mycobacterium tuberculosis, Mycobacterium paratuberculosis, Salmonella* spp., *Yersinia enterocolitica, Brucella* spp., *Staphylococcus* spp., *Lactobacillus casei, Mycobacterium avium* subspecies, *Staphylococcus aureus, Streptococcus* spp., *Enterococcus* spp., or *Entrerobacter* spp.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

DETAILED DESCRIPTION OF THE EMBODIMENTS

Figure 1:
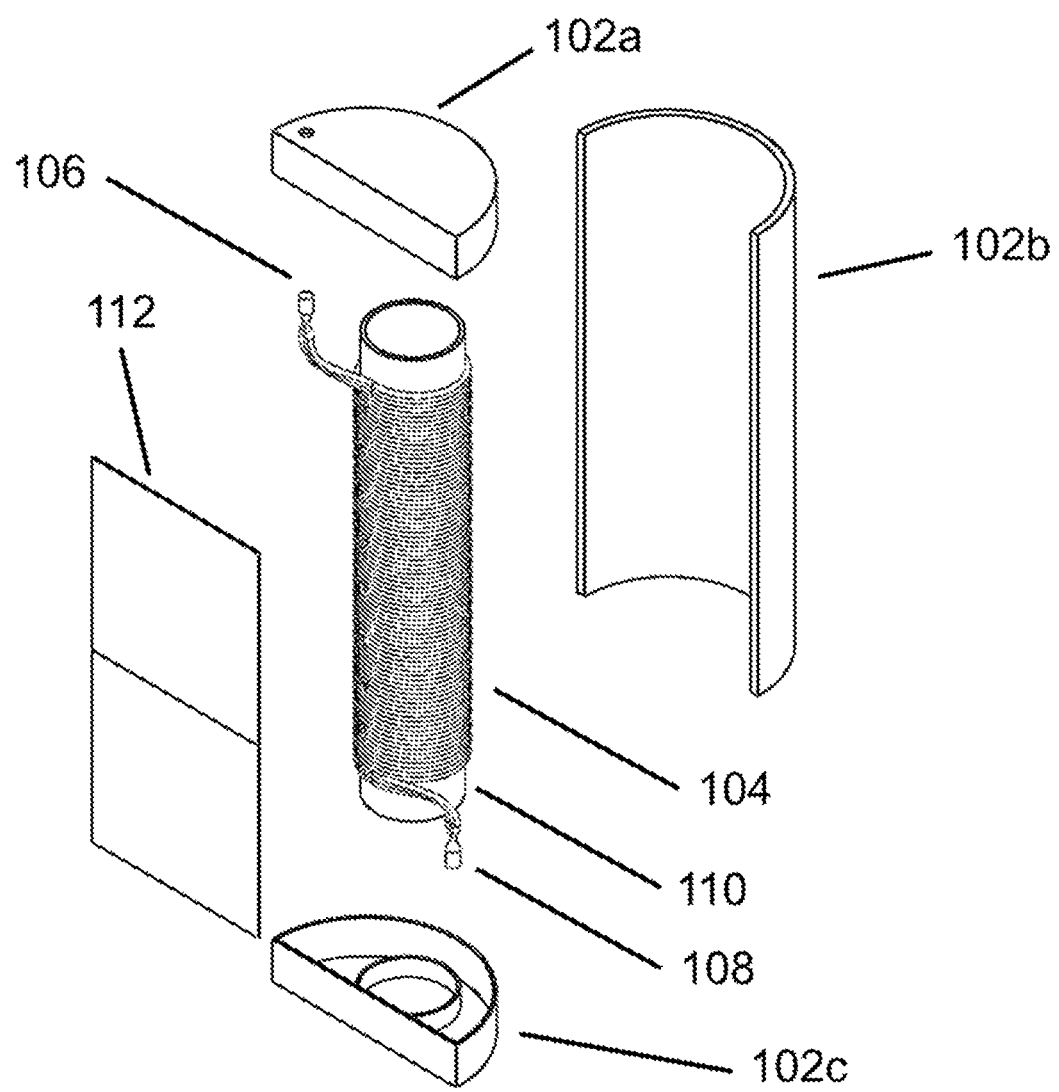
FIG. 1 shows an explosion view of an embodiment of the present invention, showing a reactor housing, spiral-shaped tubes comprising an inlet and an outlet, a pillar, and a filter.
Figure 5:
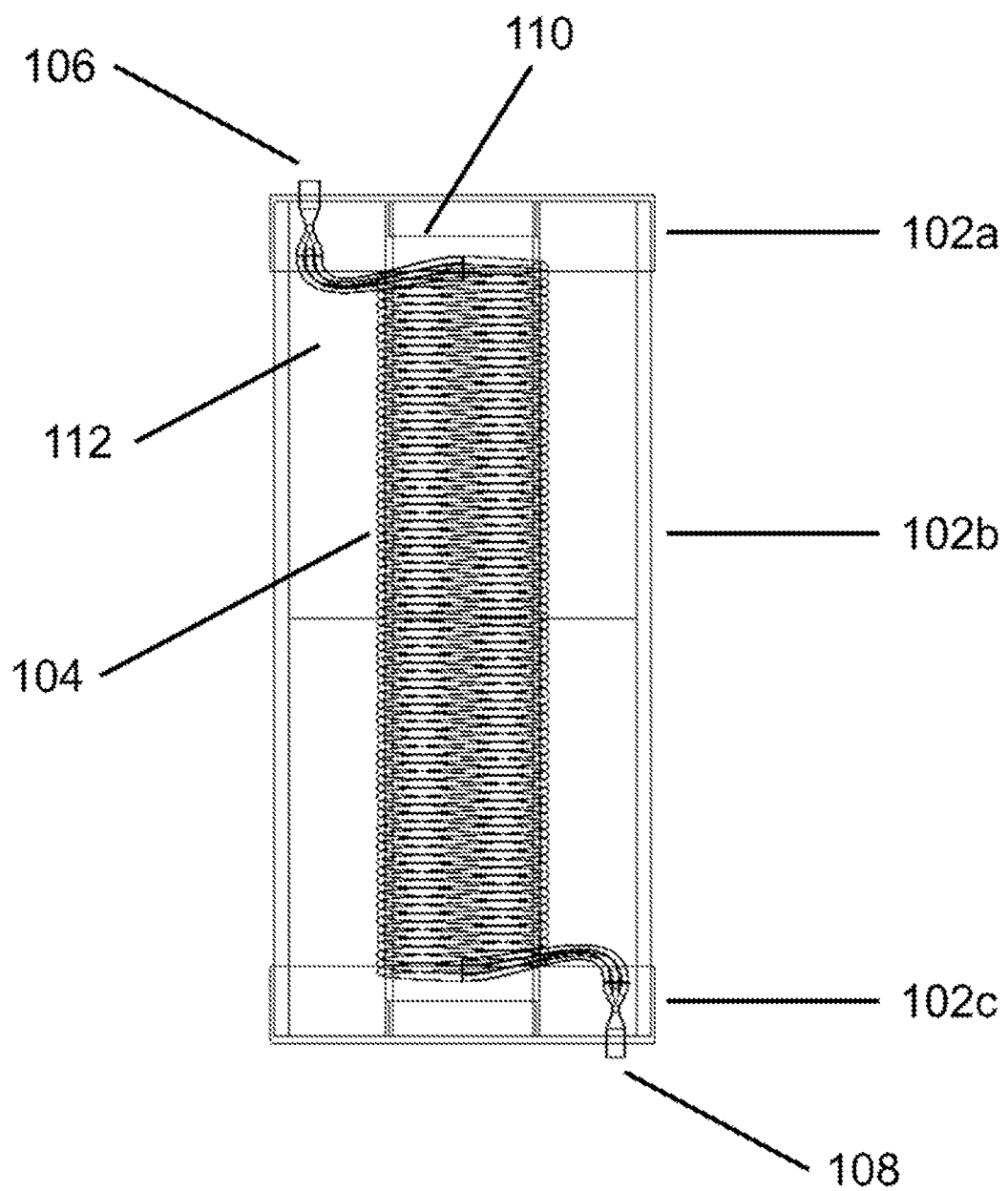
FIG. 5 shows a see-through front view of an embodiment of the present invention, showing a reactor housing, a spiral-shaped tube comprising an inlet and an outlet, a pillar, and a filter.
Figure 6:
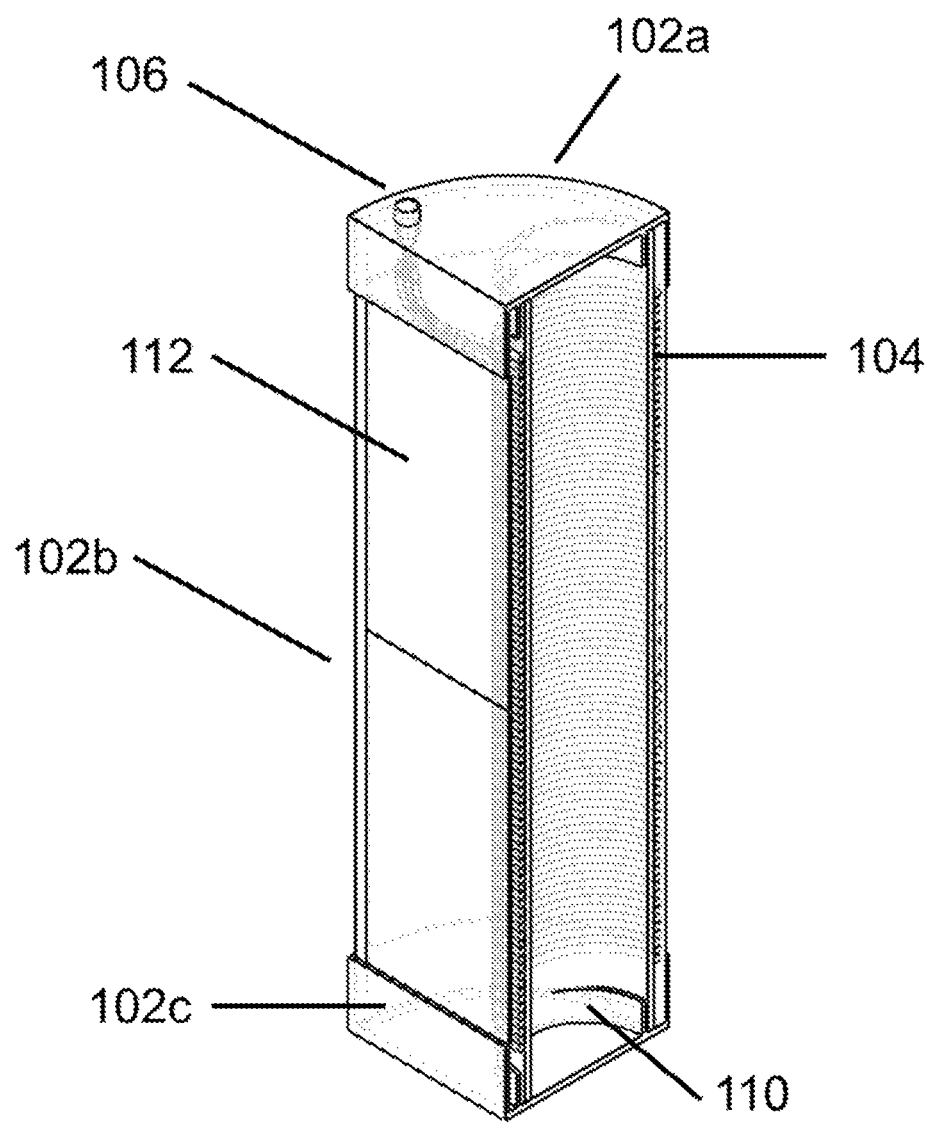
FIG. 6 shows a cut-through side view of an embodiment of the present invention, showing a reactor housing, a spiral-shaped tube comprising an inlet and an outlet (not shown), a pillar, and a filter. The cut is made down the middle of the reactor housing.

The FIGS. 1, 5, and 6 shows different views of an embodiment of a photo bioreactor for cold pasteurization of liquid food products. The photo bioreactor comprises a spiral-shaped tube 104 extending from an inlet end 106 to an outlet end 108 creating a fluidic pathway. The spiral-shaped tube 104 is coiled around a pillar 110.

The photo bioreactor further comprises a reactor housing 102a, 102b, 102c, which comprises three parts; a first part 102a positioned on the top of the photo bioreactor in FIG. 1, a second part constituting the side of the housing, and a third part positioned at the lower side of the photo bioreactor.

A filter 112 positioned between outside the spiral-shaped tube 104 is also shown in FIG. 1. The filter 112 prevents light above a wavelength of 300 nm from reaching the spiral-shaped tube 104.

The filter 112 is shown as see-through filter in FIG. 5. In FIG. 6, the shown cut is made down the middle of the reactor housing 102a, 102b, and 102c.

The photo bioreactor shown in FIGS. 1, 5 and 6 are examples of photo bioreactors where the liquid food product flows overall vertically through the one or more spiral-shaped tube 104 when observing from inlet end 106 to outlet end 108.

Figure 2:
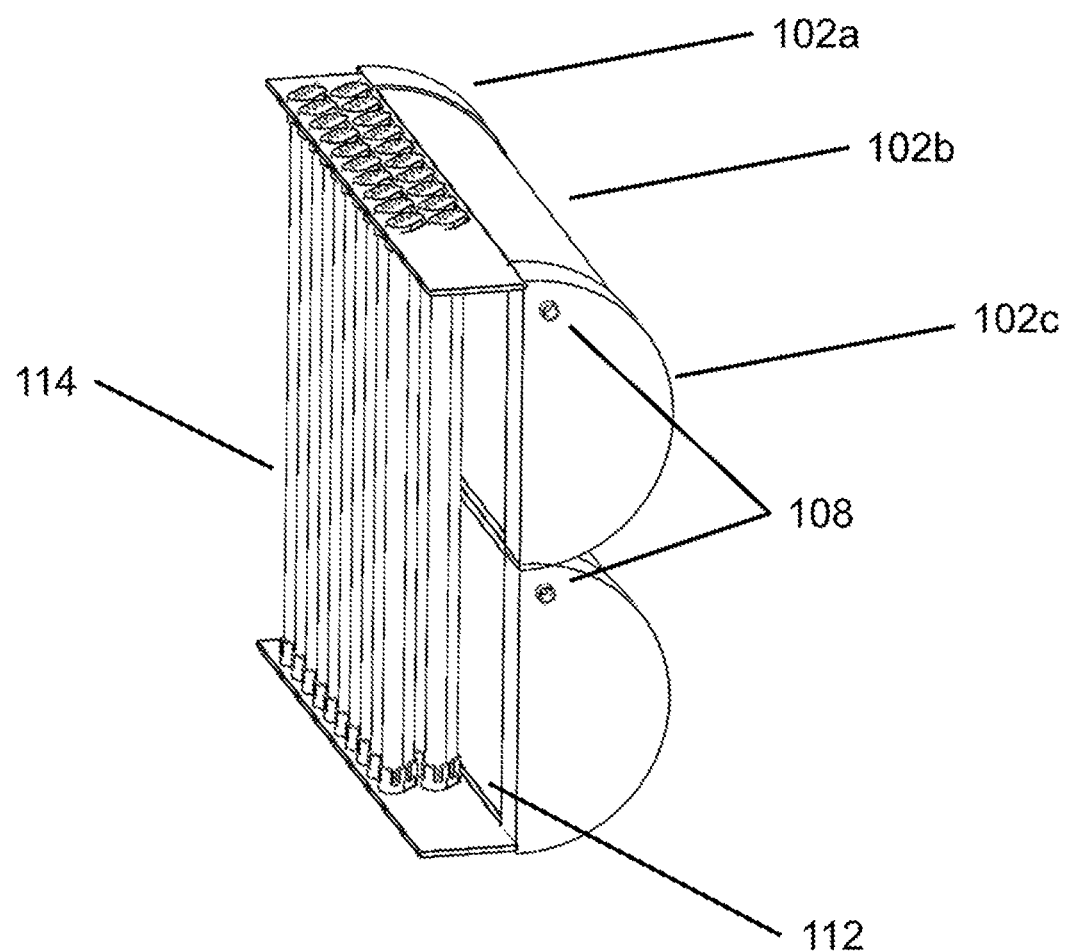
FIG. 2 shows a side view of an embodiment of the present invention, showing two reactor housings, two outlets, two filters, and multiple light sources.
Figure 3:
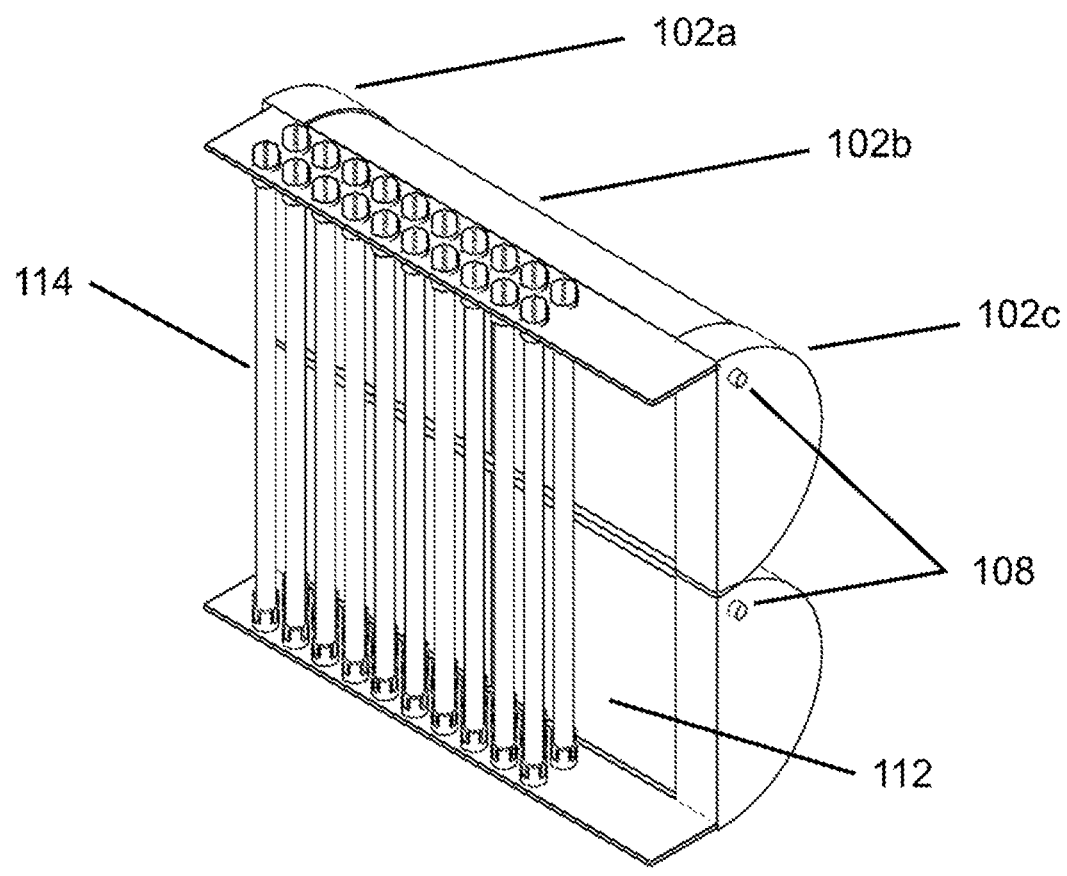
FIG. 3 shows a side view of an embodiment of the present invention, showing two reactor housings, two outlets, two filters, and multiple light sources.
Figure 4:
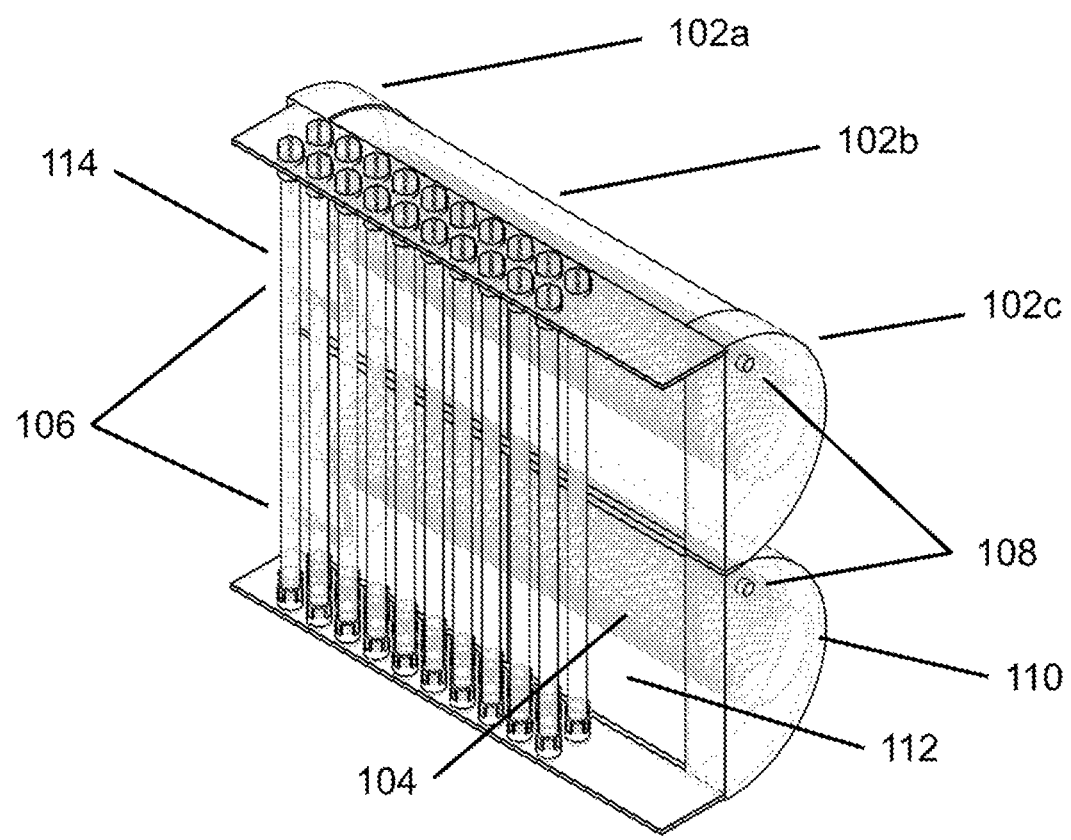
FIG. 4 shows a see-through side view of an embodiment of the present invention, showing two reactor housings (parts of reactor housing are see-through), two outlets, two filters (filters are see-through), and multiple light sources.

The FIGS. 2-4 shows an alternative embodiment of the photo bioreactor for cold pasteurization of liquid food products comprising similar elements as identified and discussed in connection with FIGS. 1, 5 and 6.

In the embodiment in FIGS. 2-4, multiple light sources 114 is utilized for illuminating two spiral-shaped tubes 104. The light sources 114 emit light in a wavelength range between 180-300 nm. In FIGS. 2-4, two filters 112 positioned between the light sources 114 and the two spiral-shaped tubes 104 included in the photo bioreactor.

The two filters 112 are shown as see-through filters in FIG. 4. Additionally, two spiral-shaped tubes 104 comprising inlets 106 and outlets 108, and the pillars 110 are visible inside the reactor housing 102a, 102b, and 102c in FIG. 4.

The photo bioreactor shown in FIGS. 2-4 are examples of photo bioreactors where the liquid food product flows overall horizontally through the one or more spiral-shaped tube 104 when observing from inlet end 106 to outlet end 108.

Figure 7:
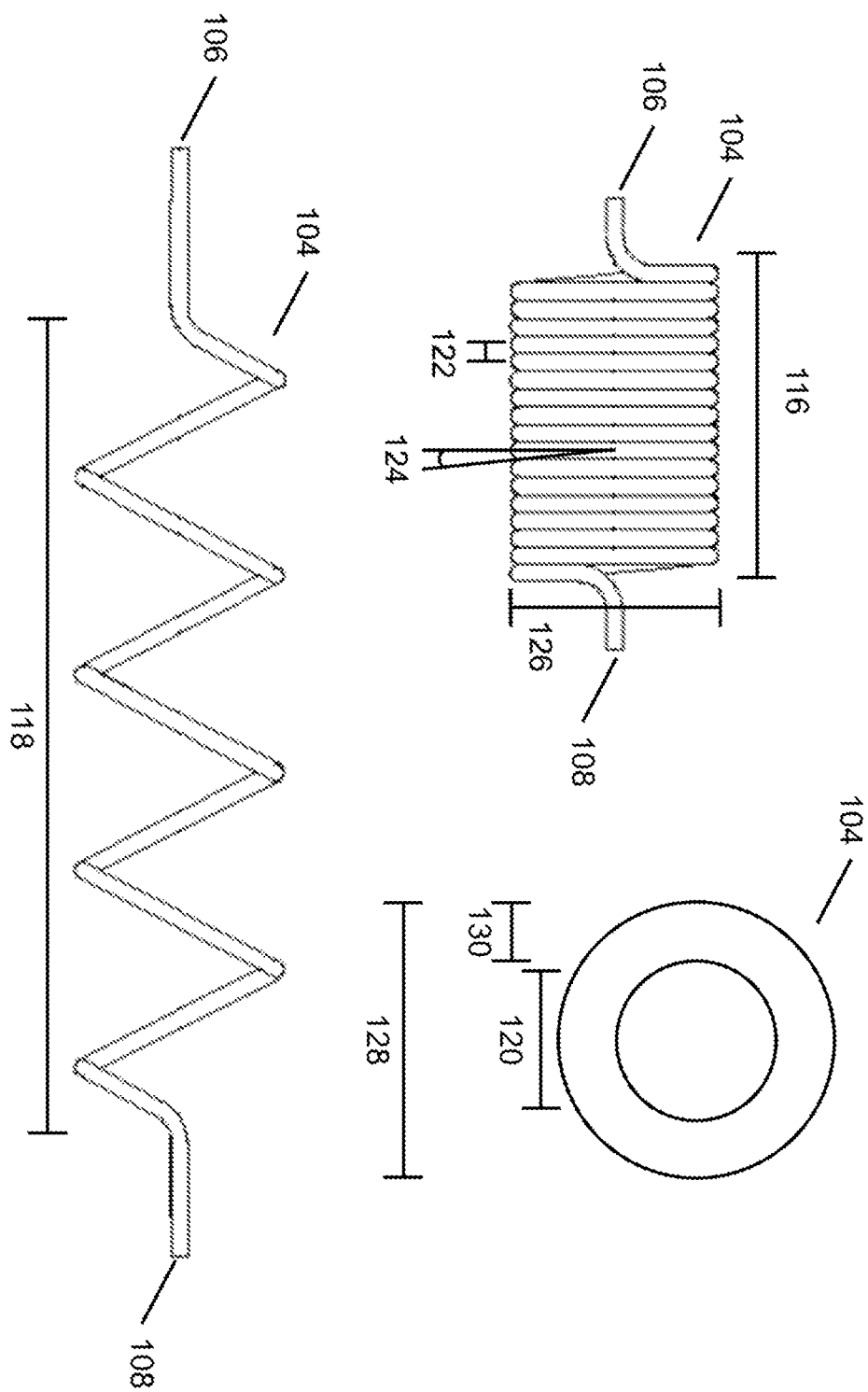
FIG. 7 shows a schematic illustration of different parts and measurements of specific embodiments of the present invention.

FIG. 7 shows spiral-shaped tubes 104 with inlet 106 and outlet 108 according to the invention. The compressed length of the spiral-shaped tube 116, the extension/free length of the spiral-shaped tubes 118, the inner tube diameter 120, the pitch 122, the coil angle 124, the coil diameter 126, the outer tube diameter 128, and the wall thickness 130 are all illustrated in FIG. 7.

Figure 8:
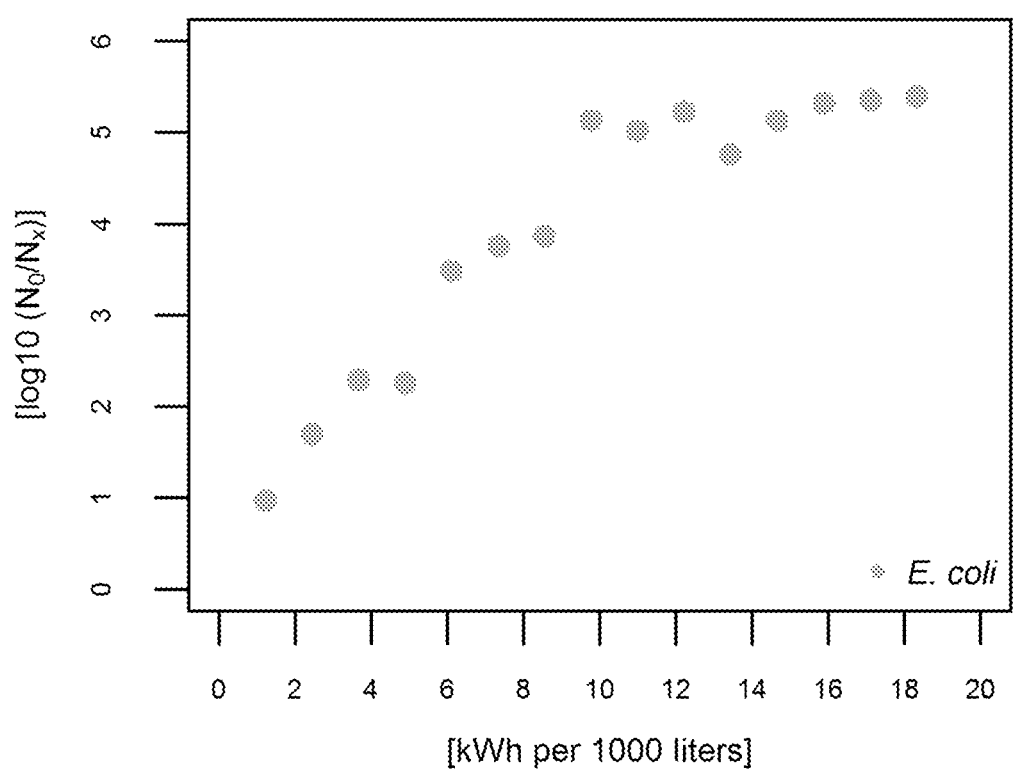
FIG. 8 shows an investigation of the amount of energy required from the light source to obtain inactivation or reduction of the biological contaminant.

FIG. 8 shows the investigation of the amount of energy required from the light source to obtain inactivation or reduction of the biological contaminant.

Figure 9:
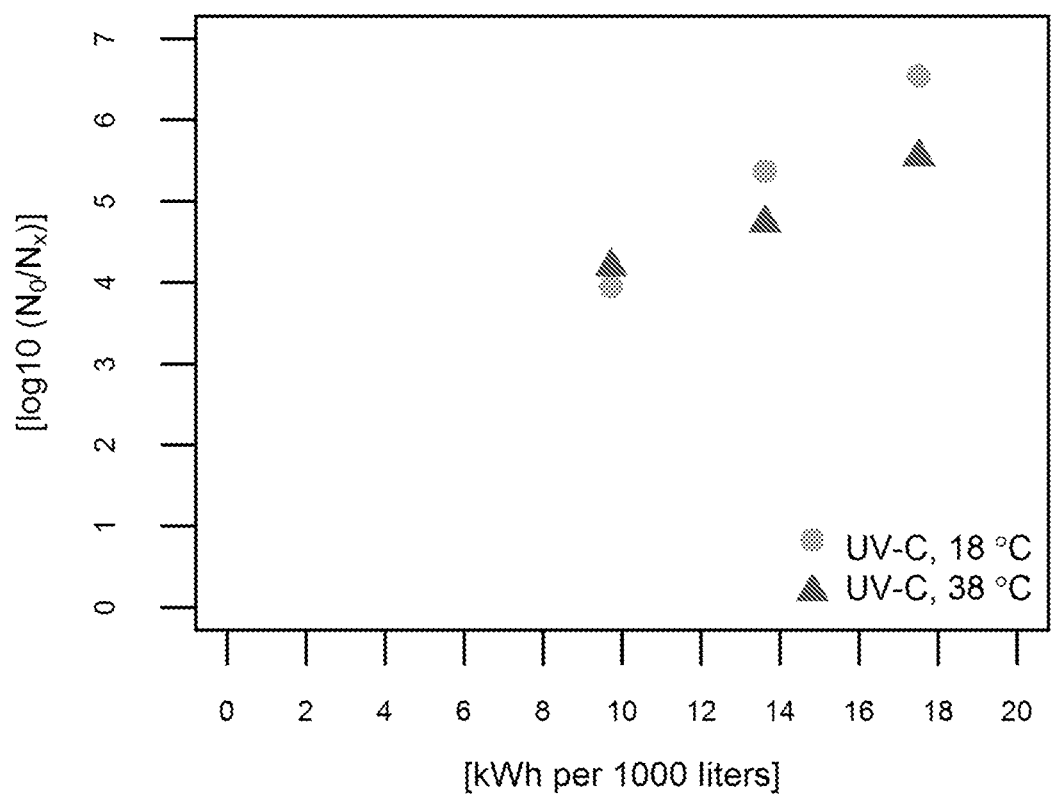
FIG. 9 shows an investigation of the difference in the current invention when varying the temperature from 18 degrees centigrade to 38 degrees centigrade.

FIG. 9 shows the investigation of the difference in the current invention when varying the temperature from 18 degrees centigrade to 38 degrees centigrade.

Figure 10:
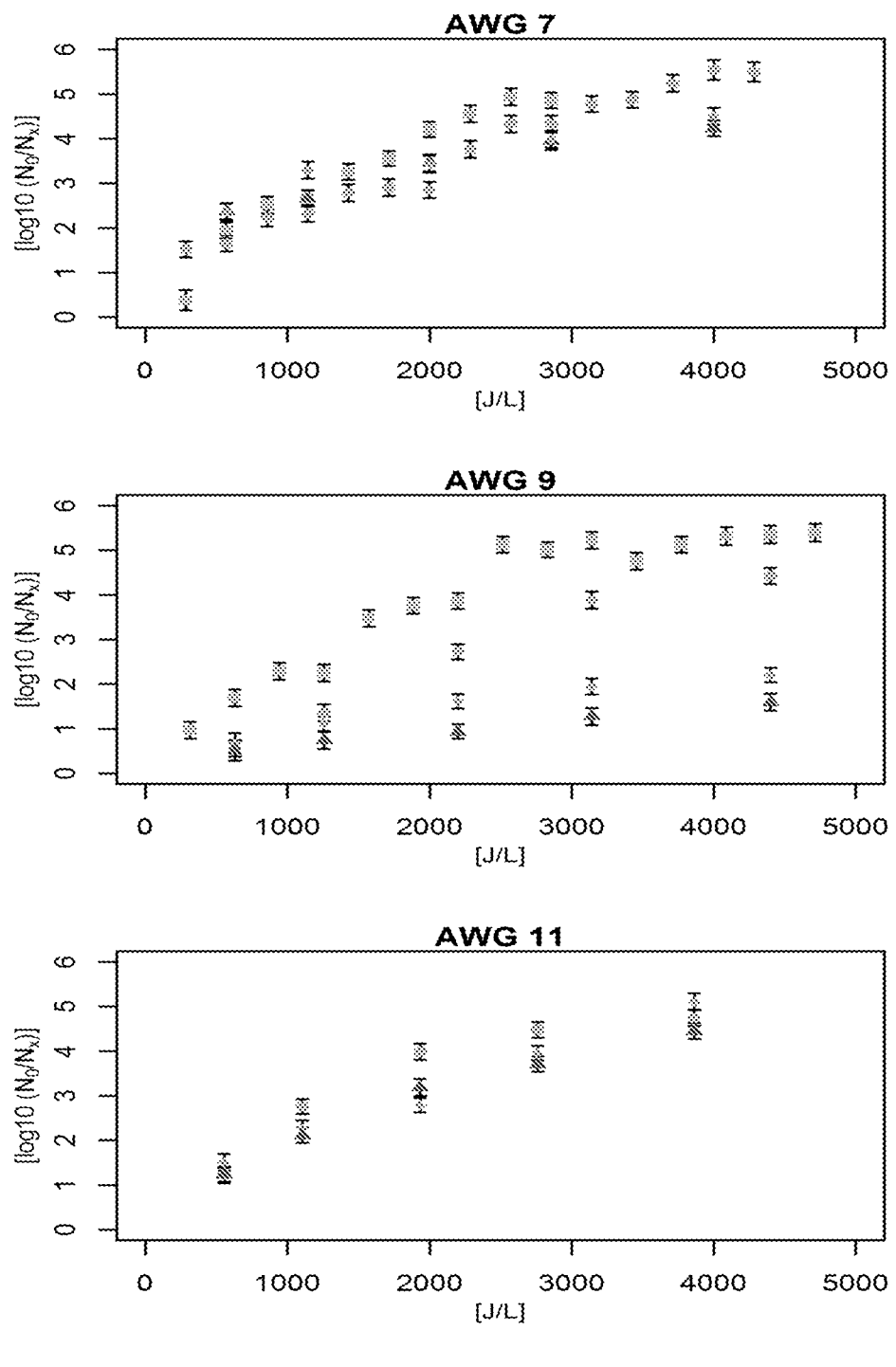
FIG. 10 shows an investigation of the current invention when varying the flow rate of the liquid at three different tube sizes.

FIG. 10 shows the investigation of the current invention when varying the flow rate of the liquid at three different tube sizes.

Figure 11:
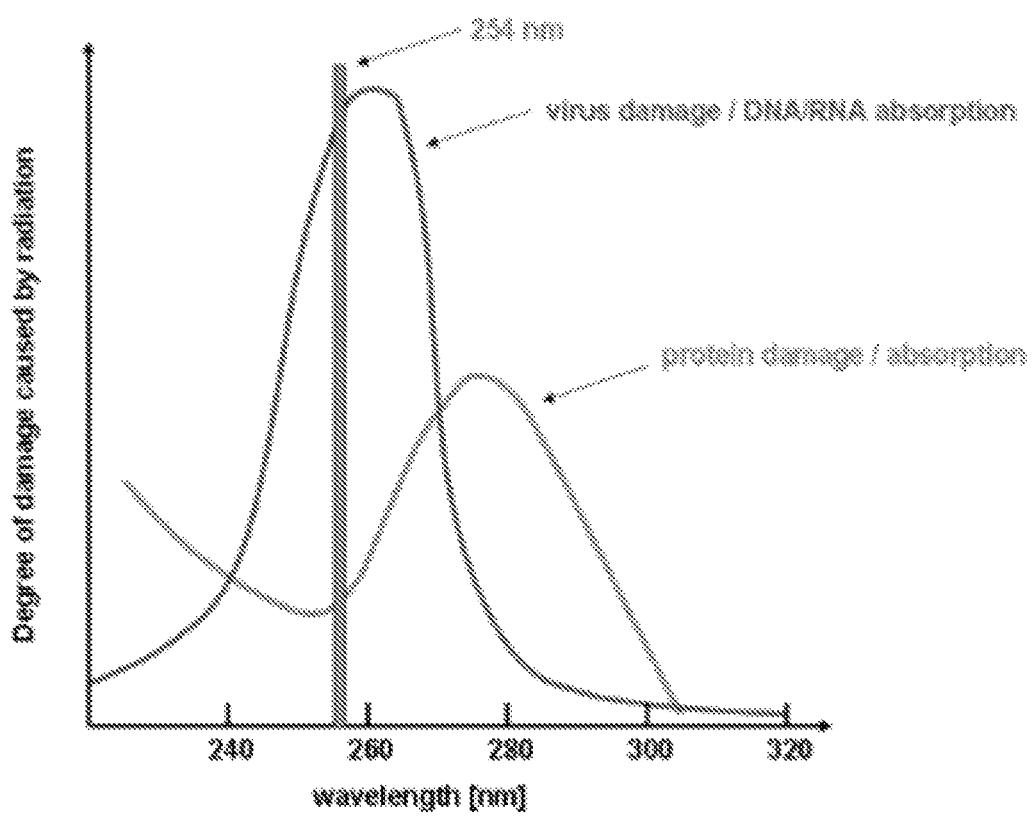
FIG. 11 shows a degree of damages caused by radiation in virus versus protein at different wavelengths (220-320 nm).

FIG. 11 shows the degree of damages caused by radiation in virus versus protein at different wavelengths (220-320 nm).

EXAMPLES

General Experimental Procedure

The effects of tube diameter and flow rate were investigated using UHT whole milk spiked with *Escherichia coli* to a concentration of minimum 2.7E6 per millilitre (determined using the most probable number method).

One litre UHT whole milk were transferred to a sterilized blue cap flask and added 1 ml of *Escherichia coli* media, achieving a desired minimum concentration of at least 2.7E6/ml. The spiked milk was circulated in the UV-reactor and samples were taken at intervals, when desired UV-C doses were achieved. The spiked milk was mixed constantly throughout the experiment using a magnetic stirrer.

For each specific flowrate and tube size a new batch of 1 litre UHT whole milk spiked with *Escherichia coli* to a minimum concentration of 2.7E6/ml was prepared.

The UV-reactor consisted of a FEP tube coiled around a 28 mm quartz glass. Within the quartz glass a 75 W germicidal lamp with a peak radiation at 253.7 nm was placed. The tested tube sizes were AWG (American wire gauge) 7, 9, and 11 and the flowrates investigated were 200, 300, 600 and 1000 ml per minute.

The milk was circulated using a rotary vane pump and exposed in the UV-reactor for a period of time before samples of 20 ml were taken using sterilized pipettes and transferred to a sterilized blue cap flask. The milk was circulated in the system, with the lamp off prior to each experiment and a sample was taken to establish the start concentration. The milk temperature was 24 to 25° C. at the start of each experiment and 34 to 43° C. at the end of each experiment.

After each experiment, the system went through a CIP (clean-in-place) procedure, first flushing the system using demineralised water for 10 minutes, followed by 40 minutes of circulating a 1% NaOH solution at 65° C. Followed by flushing the system for 10 minutes using demineralised water. After which a 0.5% $HNO_3$ solution at 60° C. were circulated in the system for 40 minutes. Finally, the system was rinsed for 20 minutes using demineralised water.

The samples were transferred to a sampling station in a laminar biosafety cabinet immediately after the experiment ended, where they were treated using the MPN method following Jarvis et al. [Jarvis, B. et al., Journal of Applied Microbiology, 2010, 109, 1660-1667].

After two days in an incubator at 35° C. the number of positive test tubes was counted and the bacteria concentrations calculated.

Example 1

Experimental example 1 investigates the amount of energy required from a pump and the light source to obtain inactivation or reduction of the biological contaminant. The tested tube size is AWG 9 and the flowrate investigated is 700 ml per minute.

As can be seen in FIG. 8, by using a small amount of light energy (around 1.2 kWh per 1,000 liter liquid) a 1-$\text{Log}_{10}$ reduction is obtained. When increasing the light energy used the Logo reduction is also increasing until a plateau is obtained from 10 kWh per 1,000 liter liquid with a reduction of around 5-$\text{Log}_{10}$.

Example 2

Experimental example 2 investigates the difference in the current invention when varying the temperature from 18 degrees centigrade to 38 degrees centigrade. The tested tube size is AWG 9 and the flowrate investigated is 700 ml per minute. As shown in FIG. 9, the difference in $\log_{10}$ reduction is similar around 10 kWh per 1,000 liter liquid. However, when the energy used is increased, the $\log_{10}$ reduction between 18 degrees centigrade and 38 degrees centigrade start to be significant. At energies of around 18 kWh per 1,000 liter liquid the $\log_{10}$ reduction is 5.5 for 38 degrees centigrade, while it is 6.5 for 18 degrees centigrade, which corresponds to 1-$\log_{10}$ reduction in difference.

Example 3

Experimental example 3 investigates the current invention when varying the flow rate of the liquid at three different tube sizes. The tested tube sizes were AWG 7, 9, and 11 and the flowrates investigated were 200, 300, 600 and 1000 ml per minute.

The temperature is kept between 24 and 43 degrees centigrade. As can be observed in FIG. 10, depending on the tube size, the setup is optimal at different flowrates.

Using a tube size of AWG 7 there is a small difference between flowrates. However, this difference is most predominant when analyzing at high energy exposure (around 4,000 J per liter liquid) where a 1-$\log_{10}$ difference is observed between flowrates of 200-300 ml/min versus flowrates of 600-1,000 ml/min.

Using a tube size of AWG 9 there is a large difference between flowrates. This difference is largest when analyzing at high energy exposure (around 4,500 J per liter liquid) where a 3-$\log_{10}$ difference is observed between flowrates of 200-300 ml/min versus flowrates of 600-1,000 ml/min.

Using a tube size of AWG 11 there is a very small difference between flowrates. However, this difference is negligible when analyzing at high energy exposure (around 4,000 J per liter liquid).

REFERENCES

102*a* First part of reactor housing
102*b* Second part of reactor housing
102*c* Third part of reactor housing
104 Spiral-shaped tubes
106 Inlet
108 Outlet
110 Pillar
112 Filter
114 Light source
116 Compressed length
118 extension/free length
120 Inner tube diameter
122 Pitch
124 Coil angle
126 Coil diameter
128 Outer tube diameter
130 Wall thickness

The invention claimed is:

1. A photo bioreactor for pasteurization of liquid food products, the photo bioreactor comprising:
   a. one or more spiral-shaped tubes extending from an inlet end to an outlet end creating a fluidic pathway; and
   b. one or more light sources illuminating the one or more spiral-shaped tubes, wherein the one or more light sources emit light in a wavelength range between 180-300 nm and light above a wavelength of 300 nm;
   wherein the photo bioreactor further comprises one or more filters positioned between the one or more light sources and the one or more spiral-shaped tubes, wherein the one or more filters prevent the light above a wavelength of 300 nm from reaching the one or more spiral-shaped tubes.

2. The photo bioreactor according to claim 1, wherein a fluid movement through the one or more spiral-shaped tubes creates a Dean Vortex flow, laminar flow, or turbulent flow.

3. The photo bioreactor according to claim 1, wherein the one or more spiral-shaped tubes have an inner tube diameter between 1 mm and 10 mm.

4. The photo bioreactor according to claim 1, wherein the one or more spiral-shaped tubes have a pitch between 2 and 8 mm wherein the pitch is the distance from center to center of the one or more spiral-shaped tubes after one turn/coil of the one or more spiral-shaped tubes.

5. The photo bioreactor according to claim 1, wherein the one or more spiral-shaped tubes have a coil angle between 1 and 6°, wherein the coil angle is measured between the one or more spiral-shaped tubes and a straight direction compared to the inlet end to the outlet end creating the fluidic pathway.

6. The photo bioreactor according to claim 1, wherein the one or more spiral-shaped tubes have a coil diameter between 20 and 150 mm, wherein the coil diameter is a distance from outer end to outer end of the one or more spiral-shaped tubes after a half turn/coil of the one or more spiral-shaped tubes.

7. The photo bioreactor according to claim 1, wherein the one or more spiral-shaped tubes are coiled around a pillar.

8. The photo bioreactor according to claim 7, wherein the pillar is made of a reflective material.

9. The photo bioreactor according to claim 1, wherein the one or more spiral-shaped tubes are made of a polymeric or quartz glass material being ultraviolet light transparent.

10. The photo bioreactor according to claim 1, wherein the one or more light sources are coupled to one or more fibers guiding the 180-300 nm light from the one or more light sources to the one or more spiral-shaped tubes.

11. The photo bioreactor according to claim 1, further comprising a reactor housing, wherein the one or more spiral-shaped tubes, the one or more light sources, and the one or more filters are enclosed inside the reactor housing.

12. The photo bioreactor according to claim 1, wherein the photo bioreactor further comprises a cooler that air cools the one or more light sources.

13. The photo bioreactor according to claim 1, wherein the photo bioreactor further comprises a control unit and the control unit comprises electronic temperature control and flow control.

14. The photo bioreactor according to claim 1, wherein the photo bioreactor further comprises a control unit and the control unit automatically controls a lamp temperature and a flow speed of a liquid through the fluidic pathway.

\* \* \* \* \*